United States Patent
Fu

(10) Patent No.: US 7,211,532 B2
(45) Date of Patent: *May 1, 2007

(54) ALKALI ION CONDUCTIVE GLASS-CERAMICS AND ELECTRIC CELLS AND GAS SENSORS USING THE SAME

(75) Inventor: Jie Fu, Sagamihara (JP)

(73) Assignee: Kabushiki Kaisha Ohara, Kanagawa-ken (JP)

( * ) Notice: Subject to any disclaimer, the term of this patent is extended or adjusted under 35 U.S.C. 154(b) by 750 days.

This patent is subject to a terminal disclaimer.

(21) Appl. No.: 10/462,450

(22) Filed: Jun. 16, 2003

(65) Prior Publication Data

US 2003/0205467 A1    Nov. 6, 2003

Related U.S. Application Data

(63) Continuation of application No. 09/614,948, filed on Jul. 12, 2000, now abandoned, which is a continuation of application No. 08/923,233, filed on Sep. 4, 1997, now abandoned, which is a continuation-in-part of application No. 08/741,704, filed on Oct. 31, 1996, now Pat. No. 5,702,995.

(30) Foreign Application Priority Data

| Nov. 15, 1995 | (JP) | ................................. 7-320971 |
| Apr. 12, 1996 | (JP) | ................................. 8-115694 |
| Feb. 6, 1997 | (JP) | ................................. 9-38303 |

(51) Int. Cl.
  *C03C 10/02* (2006.01)
  *C03C 4/14* (2006.01)

(52) U.S. Cl. .................. 501/10; 204/429; 429/320; 429/322

(58) Field of Classification Search .................. 501/10; 204/429; 429/320, 322
  See application file for complete search history.

(56) References Cited

U.S. PATENT DOCUMENTS

| 4,223,077 | A | * | 9/1980 | Taylor ..................... 429/321 |
| 4,507,369 | A | * | 3/1985 | Badzioch ................. 429/104 |
| 4,874,724 | A | * | 10/1989 | Beall et al. ................ 501/10 |
| 4,985,317 | A | * | 1/1991 | Adachi et al. ............. 429/322 |
| 5,702,995 | A | * | 12/1997 | Fu ............................ 501/10 |
| 6,030,909 | A | * | 2/2000 | Fu ............................ 501/10 |
| 6,475,677 | B1 | * | 11/2002 | Inda et al. ................ 429/304 |
| 6,485,622 | B1 | * | 11/2002 | Fu ........................... 204/421 |

FOREIGN PATENT DOCUMENTS

JP      5-139781      *  6/1993

* cited by examiner

*Primary Examiner*—Karl Group
(74) *Attorney, Agent, or Firm*—Hedman & Costigan P.C.; James V. Costigan

(57) ABSTRACT

There are provided glass-ceramics having a high lithium ion conductivity which include in mol %:

| $P_2O_5$ | 38–40% |
| $TiO_2$ | 25–45% |
| $M_2O_3$ (where M is Al or Ga) | 5–15% |
| $Li_2O$ | 10–20% | and contain $Li_{1+X}(Al, Ga)_X Ti_{2-X}(PO_4)_3$ (where $0<X<0.8$) as a main crystal phases. There are also provided glass-ceramics having a high lithium ion conductivity which include in mol %:

| $P_2O_5$ | 26–40% |
| $SiO_2$ | 0.5–12% |
| $TiO_2$ | 30–45% |
| $M_2O_3$ (where M is Al or Ga) | 5–10% |
| $Li_2O$ | 10–18% | and contain $Li_{1+X+Y}M_X Ti_{2-X} Si_Y P_{3-Y} O_{12}$ (where $0<X\leq0.4$ and $0<Y\leq0.6$) as a main crystal phase. There are also provided solid electrolytes for an electric cell and a gas sensor using alkali ion conductive glass-ceramics, and a solid electric cell and a gas sensor using alkali ion conductive glass-ceramics as a solid electrolyte.

5 Claims, 3 Drawing Sheets

ALKALI ION CONDUCTIVE GLASS-CERAMICS AND ELECTRIC CELLS AND GAS SENSORS USING THE SAME

This application is a continuation of Ser. No. 09/614,948, filed Jul. 12, 2000, now abandoned, which is a continuation of Ser. No. 08/923,233, filed Sep. 4, 1997, abandoned, which is a continuation in part of Ser. No. 08/741,704, filed Oct. 31, 1996, now U.S. Pat. No. 5,702,995, which claims priority under 35 U.S.C. § 119 to Japanese Application Nos. 320971/1995, filed Nov. 15, 1995; 115694, filed Apr. 12, 1996; and 38303 filed Feb. 6, 1997.

BACKGROUND OF THE INVENTION

This invention relates to an alkali ion conductive glass-ceramics and, more particularly, to a lithium ion conductive glass-ceramics suitable for use as wholly solid electric cells, gas sensors and electrochemical devices of various types, and electric cells and gas sensors using such glass-ceramics.

Recent development in electronics has brought about high-performance electronic devices of a compact and light-weight design and, as a power source of such electronic devices, development of an electric cell of a high energy density and a long life is strongly desired for.

Lithium has the highest oxidation-reduction potential of $Li/Li^+$ of all metal elements and has the smallest mass per 1 mol and, therefore, lithium cell can provide a higher energy density than other types of cells. Moreover, if a lithium ion conductive solid electrolyte is used, this electrolyte can be made very thin and, therefore, a cell of a thin film can be formed and increase in energy density per unit volume can thereby be realized.

A lithium ion cell which has been realized to date uses an organic electrolyte solution as its electrolyte and this makes it difficult to achieve a cell of a compact design such as a thin film design. This lithium ion cell has additional disadvantages that it has likelihood of leakage of electrolyte solution and likelihood of spontaneous combustion. If this lithium ion cell is replaced by a cell employing an inorganic solid electrolyte, a wholly solid cell of a high reliability will be realized. For this reason, studies and developments of a solid electrolyte having a high conductivity have been vigorously made for realizing a wholly solid lithium cell.

Moreover, carbon dioxide gas produced by combustion of fossil fuel is a main cause of a hothouse effect which has recently become a serious problem and it has become necessary to incessantly watch the concentration of carbon dioxide gas. Therefore, establishment of a system for detecting carbon dioxide gas is a matter of increasing importance for the maintenance of a comfortable life in the future human society.

Carbon dioxide gas detection systems which are currently in use are generally of a type utilizing absorption of infrared ray. These systems however are large and costly and besides are very susceptible to contamination. For these reasons, studies have recently been actively made to develop a compact carbon dioxide gas sensor using a solid electrolyte. Particularly, many reports have been made about studies using a lithium ion sold electrolyte.

For realizing such gas sensor using solid electrolyte, development of a solid electrolyte which is highly conductive, chemically stable and sufficiently heat proof is indispensable.

Among known electrolyes, $Li_3N$ single crystal (Applied Physics letter, 30(1977) 621–22) and $LiI$-$Li_2S$—$B_2S_5$, $LiI$-$Li_2S$—$SiS_4$ and $LiI$-$Li_2S$—$B_2S_3$ glasses (Mat. Res. Bull., 18(1983) 189) have high conductivity of $10^{-3}$S/cm or over. These materials, however, have the disadvantages that preparation and handling of these materials are difficult and these materials are not sufficiently heat proof. Particularly, these materials have the fatal disadvantage that decomposition voltage of these materials is so low that, when they are used for an electrolyte of a solid cell, a sufficiently high terminal voltage cannot be obtained.

An oxide lithium solid electrolyte does not have the above described disadvantages and has a decomposition voltage which is higher than 3V and, therefore, it has possibility of usage as a wholly solid lithium cell if it exhibits a high conductivity at room temperature. It is known in the art that conductivity in an oxide glass can be increased by increasing lithium ion concentration. However, there is limitation in increase in the lithium ion concentration even if rapid quenching is employed for glass formation and conductivity of this glass at room temperature is belong $10^{-6}$S/cm at the highest.

Japanese Patent Application Laid-open Publication No. Hei-8-2239218 discloses a gas sensor using a thin film of a lithium ion conductive glass. The conductivity of this lithium ion conductive glass thin film is between $1.7\times10^{-7}$ and $6.1\times10^{-7}$. This is not a sufficiently high value and a solid electrolyte having a higher conductivity is desired for.

An oxide ceramic having the highest conductivity at room temperature is $Li_{1+X}Al_XTi_{2-X}(PO_4)_3$. When X is 0.3, the conductivity thereof is $7\times10^{-4}$S/cm at room temperature (J. Electrochem. Soc., 137 (1990) 1023). Oxide ceramics are superior in conductivity to glasses but have the disadvantages that they require a troublesome process for manufacturing and that they are difficult to form, particularly to a thin film.

In short, the prior art lithium ion solid electrolytes have the problems that they are either low in codutivity, hard to handle, hard to form to a compact design such as a thin film.

It is, therefore, an object of the invention to provide glass-ceramics which have solved these problems and exhibit a very high alkali ion conductivity in the order of $10^{-3}$S/cm at room temperature.

It is another object of the invention to provide an alkali cell and a gas sensor of a high performance by utilizing such glass-ceramics.

SUMMARY OF THE INVENTION

As described above, $Li_{1+X}Al_XTi_{2-X}(PO_4)_3$ ceramics exhibit conductivity of $10^{-4}$S/cm or over at room temperature. These ceramics, however, have pores and a large grain boundary which can not be eliminated completely and existence of these pores and grain boundary results in a decrease in conductivity. If, therefore, glass-ceramics including the above crystal are provided, there will be no pores and the grain boundary will be improved and, as a result, a solid electrolyte having a higher conductivity is expected to be provided. Besides, glass-ceramics which share a feature of glass can be easily formed into various shapes including a thin film by utilizing this feature of glass. For these reasons, glass-ceramics are considered to have practical advantages over ceramics made by sintering.

As a result of studies and experiments made by the inventor of the present invention on the basis of the above described basic concept, the inventor has succeeded in obtaining glass-ceramics having a very high lithium ion conductivity in the order of $10^{-3}$S/cm at room temperature by producing glasses including the ingredients of the above described crystal and causing the crystal phase to grow from these glasses by heat treating these glasses.

A lithium ion conductive glass-ceramics achieving the above object of the invention comprise in mol %:

| | |
|---|---|
| $P_2O_5$ | 38–40% |
| $TiO_2$ | 25–45% |
| $M_2O_3$ (where M is Al or Ga) | 5–15% |
| $Li_2O$ | 10–20% | and contains $Li_{1+X}(Al, Ga)_X Ti_{2-X}(PO_4)_3$ (where 0<X<0.8) as a main crystal phase.

In one aspect of the invention, said glass-ceramics comprise in mol %:

| | |
|---|---|
| $P_2O_5$ | 38–40% |
| $TiO_2$ | 30–45% |
| $Al_2O_3$ | 5–15% |
| $Li_2O$ | 10–16%. |

In another aspect of the invention, said glass-ceramics comprise in mol %:

| | |
|---|---|
| $P_2O_5$ | 38–40% |
| $TiO_2$ | 25–45% |
| $Ga_2O_3$ | 5–12% |
| $Li_2O$ | 10–20%. |
| $Li_2O$ | 10–20% |

The inventor of the present invention has further succeeded in obtaining glass-ceramics having the high lithium ion conductivity in the order of $10^{-3}$S/cm at room temperature by producing glasses including ingredients of $P_2O_5$, $SiO_2$, $TiO_2$, $M_2O_3$ (where M is Al or Ga) and $Li_2O$ and causing a crystal phase of a conductive crystal $Li_{1-X+Y}M_X Ti_{2-X} Si_Y P_{3-Y}O_{12}$ to grow from the glasses by heat treating these glasses.

Therefore, in another aspect of the invention, there is provided a lithium ion conductive glass-ceramics comprising in mol %:

| | |
|---|---|
| $P_2O_5$ | 26–40% |
| $SiO_2$ | 0.5–12% |
| $TiO_2$ | 30–45% |
| $M_2O_3$ (where M is Al or Ga) | 5–10% |
| $Li_2O$ | 10–18% | and containing $Li_{1+X+Y}M_X Ti_{2-X} Si_Y P_{3-Y}O_{12}$ (where $0<X \leq 0.4$ and $0<Y \leq 0.6$) as a main crystal phase.

In another aspect of the invention, said glass-ceramics comprise in mol %:

| | |
|---|---|
| $P_2O_5$ | 26–40% |
| $SiO_2$ | 0.5–12% |
| $TiO_2$ | 32–45% |
| $Al_2O_3$ | 5–10% |
| $Li_2O$ | 10–18%. |

In another aspect of the invention, said glass-ceramics comprise in mol %:

| | |
|---|---|
| $P_2O_5$ | 25–40% |
| $SiO_2$ | 0.5–12% |
| $TiO_2$ | 32–45% |
| $Ga_2O_3$ | 5–10% |
| $Li_2O$ | 10–18%. |

According to the invention, there are provided lithium ion conductive glass-ceramics which exhibit a very high conductivity in the order of $10^{-3}$S/cm at room temperature. In addition to having the high conductivity, the glass-ceramics made according to the invention have such an excellent formability that they can be easily formed into various shapes including a thin film, and they are thermally and chemically stable so that they are suitable for use as electrolytes of wholly solid cells, sensors and other various electrochemical devices.

In another aspect of the invention, there is provided a solid electrolyte for an electric cell characterized in that an alkali ion conductive glass-ceramic is used as said solid electrolyte.

In another aspect of the invention, there is provided a solid electrolyte for an electric cell characterized in that a lithium ion conductive glass-ceramic is used as said solid electrolyte.

In another aspect of the invention, there is provided a solid electrolyte for an electric cell characterized in that a lithium ion conductive glass-ceramic as defined in any of claims 1–6 is used as said solid electrolyte.

In another aspect of the invention, there is provided a solid electric cell characterized in that an alkali ion conductive glass-ceramic is used as a solid electrolyte.

In another aspect of the invention, there is provided a solid electric cell characterized in that a lithium ion conductive glass-ceramic is used as a solid electrolyte.

In another aspect of the invention, there is provided a solid electric cell characterized in that a lithium ion conductive glass-ceramic as defined in any of claims 1–6 is used as a solid electrolyte.

In another aspect of the invention, there is provided a solid electrolyte for a gas sensor characterized in that an alkali ion conductive glass-ceramic is used as said solid electrolyte.

In another aspect of the invention, there is provided a solid electrolyte for a gas sensor characterized in that a lithium ion conductive glass-ceramic is used as said solid electrolyte.

In another aspect of the invention, there is provided a solid electrolyte for a gas sensor characterized in that a lithium ion conductive glass-ceramic as defined in any of claims 1–6 is used as said electrolyte.

In another aspect of the invention, there is provided a gas sensor characterized in that an alkali ion conductive glass-ceramic is used as a solid electrolyte.

In another aspect of the invention, there is provided a gas sensor characterized in that a lithium ion conductive glass-ceramic is used as a solid electrolyte.

In still another aspect of the invention, there is provided a gas sensor characterized in that a lithium ion conductive glass-ceramic as defined in any of claims 1–6 is used as a solid electrolyte.

DETAILED DESCRIPTION OF THE INVENTION

The compoisitions of the glass-ceramics made according to the invention are expressed on the basis of compositions of oxides as in their base glasses. The above described content ranges of the respective ingredients have been selected for the reasons stated below.

In the ternary system $P_2O_5$—$TiO_2$—$Li_2O$, glass forming region exists in a very narrow range and the composition identical with that of $Li_{1+x}Al_xTi_{2-x}(PO_4)_3$ does not form glass when X is 0 (Bulletin of the Chemical Society of Japan, 51(1978) 2559). In the $P_2O_5$—$TiO_2$—($Al_2O_3$, $Ga_2O_3$)—$Li_2O$ system including $Al_2O_3$ or $Ga_2O_3$, a glass forming range has not been reported yet. Neither has been reported any glass-ceramic which has been prepared from such systems for obtaining a high lithium ion conductivity.

The inventor of the present invention has examined the glass forming range of the $P_2O_5$—$TiO_2$—($Al_2O_3$, $Ga_2O_3$)—$Li_2O$ system by employing a conventional glass melting method and obtained lithium ion solid electrolytes of a high conductivity which can be glassified within the following composition ranges (expressed in mol %) and can grow, as a result of heat treatment, $Li_{1+x}(Al, Ga)_xTi_{2-x}(PO_4)_3$ as a main crystal phase.

In the case of the system including $Al_2O_3$,

| | |
|---|---|
| $P_2O_5$ | 38–40% |
| $TiO_2$ | 30–45% |
| $Al_2O_3$ | 5–15% |
| $Li_2O$ | 10–16%. |

In the case of a system including $Ga_2O_3$,

| | |
|---|---|
| $P_2O_5$ | 38–40% |
| $TiO_2$ | 25–45% |
| $Ga_2O_3$ | 5–12% |
| $Li_2O$ | 10–20% |

In the case (if a system including both $Al_2O_3$ and $Ga_2O_3$,

| | |
|---|---|
| $P_2O_5$ | 38–40% |
| $TiO_2$ | 25–45% |
| $Al_2O_3$, $Ga_2O_3$ | 5–15% |
| $Li_2O$ | 10–20% |

It has been found that a glass forming region exists beyond the above described composition ranges but, after a heat treatment, an electrolyte having a high conductivity could not be obtained from such Composition range outside of the above described composition ranges. The above described composition ranges of the glass-ceramics of the invention have been determined on the basis of these experiments.

In this system, a part of Al or Ga ingredient may be replaced by one of such trivalent metal elements as B, In, Sc, Fe and Cr. In this case, however, the amount of Al or Ga replaced by such metal element should not exceed 5%. If the amount of the replaced metal element exceeds 5%, conductivity will drop significantly.

A method for manufacturing the conductive glass-ceramics of the $P_2O_5$—$TiO_2$—($Al_2O_3$, $Ga_2O_3$)—$Li_2O$ system will now be described.

Starting materials are weighed at a predetermined ratio and mixed uniformly and the mixed materials are thereafter put in a platinum crucible and heated and melted in an electric furnace. First, gas components coming from the raw materials are evaporated at 700° C. and then the temperature is raised to 1400° C. to 1450° C. and the materials are melted at this temperature for about one to two hours. Then the melt is cast onto a stainless steel plate to form a sheet glass. The resultant glass is subjected to heat treatment within the temperature range from 800° C. to 1000° C. for 10 to 72 hours and lithium ion conductive glass-ceramics containing $Li_{1+x}(Al, Ga)_xTi_{2-x}(PO_4)_3$ as a main crystal phase were thereby produced.

A heat treatment at a higher temperature within the above described temperature range will be desirable if micro cracks are not produced because a heat treatment at a higher temperature will reduce the heat treating time. Generally speaking, a heat treatment performed at a temperature which is higher by about 300° C. than a crystallization temperature of the glass will be most effective because it will provide the highest conductivity.

In the case of the glass-ceramics according to the invention made of the $P_2O_5$—$SiO_2$—$TiO_2$—($Al_2O_3$, $Ga_2O_3$)—$Li_2O$ system, the above described composition ranges have been selected because, within these composition ranges, dense glass-ceramics containing $Li_{1+X+Y}M_XTi_{2-X}Si_YP_{3-Y}O_{12}$ (where $0<X\leq0.4$, $0<Y\leq0.6$) as a main crystal phase and exhibiting a high lithium ion conductivity at room temperature were obtained by heat treating glasses of the same composition ranges. It has been found that the same crystal can be precipitated even in a composition range outside of the above described composition ranges but this crystal does not constitute a main crystal phase of a glass-ceramic produced and conductivity of this glass-ceramic is not sufficiently high.

In this system, $SiO_2$ is a very important ingredient. By adding $SiO_2$, the glass forming range is broadened and, moreover, melting property and thermal stability of the glass are improved and an excellent conductivity in the order of $10^{-3}$S/cm can be obtained.

A part of Al or Ga may be replaced by one of such trivalent metal elements such as B, In, Sc, Fe and Cr or one of such divalent metal elements as Mg and Zn. Likewise, a part of Ti may be replaced by Zr and a part of Si may be replaced by Ge. In these cases, however, the amount of Al, Ga, Ti or Si replaced by such metal element should not exceed 5%. If the amount of the replaced metal element exceeds 5%, conductivity will drop significantly.

For improving the melting property of the glass, $As_2O_3$, $Sb_2O_3$, $Ta_2O_5$, CdO or PbO may be added. The amount of such ingredient however should not exceed 3%. If the amount of such ingredient exceeds 3%, conductivity of the glass-ceramic will decrease as the amount of addition of the ingredient increases.

A method for manufacturing the conductive glass-ceramics of the $P_2O_5$—$SiO_2$—$TiO_2$—($Al_2O_3$, $Ga_2O_3$)—$Li_2O$ system wilt now be described.

Starting materials are weighed at a predetermined ratio and mixed uniformly and the mixed materials are thereafter put in a platinum crucible and heated and melted in an electric furnace. First, gas components coming from the raw materials are evaporated at 700° C. and then the temperature is raised to 1400° C. to 1500° C. and the materials are melted at this temperature for about one to two hours. Then the melt is cast onto a stainless steel plate to form a sheet glass. The glass thus produced is thereafter subjected to heat treatment by heating it under a temperature ranging from 680° C. to 800° C. for about twelve hours and subsequently heating it under a temperature which is higher by 200° C. to 350° C. for about twenty-four hours and glass-ceramics containing $Li_{1+x+y}M_xTi_{2-x}Si_yP_{3-y}O_{12}$ as a main crystal phase and having a high lithium ion conductivity is produced.

This two-step heat treatment method is applicable also to the production of the glass-ceramics of the $P_2O_5$—$TiO_2$—($Al_2O_3$, $Ga_2O_3$)—$Li_2O$ system. Conversely, the glass-ceramics of the $P_2O_5$—$SiO_2$—$Ti_{O2}$—($Al_2O_3$, $Ga_2O_3$)—$Li_2O$ system can be produced by employing the one step heat treatment method described above with respect to the glass-ceramics of the $P_2O_5$—$TiO_2$—($Al_2O_3$, $Ga_2O_3$)—$Li_2O$ system.

BRIEF DESCRIPTION OF THE DRAWINGS

In the accompanying drawings.

EXAMPLES

Figure 1:
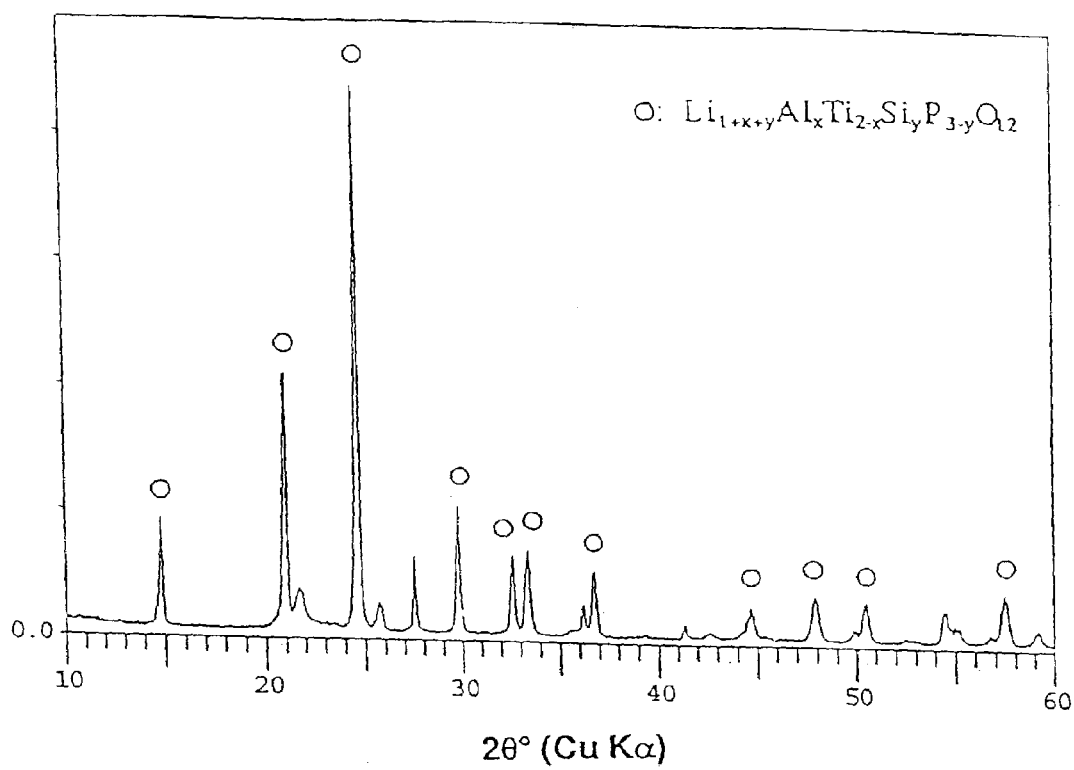
FIG. 1 is a graph showing an X-ray diffraction pattern of Example 3.

Examples of the glass-ceramics made according to the invention will now be described. It should be noted that these examples are illustrative only and the scope of the invention in no way is restricted by these examples.

Example 1

As starting materials, $NH_4H_2PO_4$, $TiO_2$, $Al(OH)_3$ and $Li_2CO_3$ were used. These starting materials were weighed to constitute a composition of $39P_2O_5$-$8.5Al_2O_3$-$39TiO_2$-$13.5Li_2O$ in mol %. The materials were mixed uniformly and then put in a platinum crucible and heated and melted in an electric furnace. First, $CO_2$, $NH_3$ and $H_2O$ coming from the raw materials were evaporated at 700° C. Then the temperature was raised to 1450° C. and the materials were melted by heating them at this temperature for 1.5 hour. Thereafter, the melt was cast onto a stainless steel plate to form a uniform sheet glass. The glass was annealed at 550° C. for two hours for removing thermal stress of the glass.

The glass thus produced was cut into specimens each having the size of 20×20 mm. The specimens of glass were polished on both surfaces and subjected to heat treatment under various heat conditions. The crystal phase which precipitated in the specimens was determined by the powder X-ray diffraction method. As a result, it was found that the precipitated crystal phase under all heat conditions was $Li_{1+x}Al_xTi_{2-x}(PO_4)_3$. Electrical conductivity of the glass-ceramic was measured within a range from $10^{-2}$–$3\times10^{+7}$ Hz by the complex impedance. Resistance of the specimens (sum of grain resistance and grain boundary resistance) was determined from the Cole-Cole Plot and the conductivity was calculated by the equation $\sigma=(t/A)(1/R)$ (where $\sigma$ is conductivity, t is thickness of the specimen, A is electrode area and R is resistance of the specimen). As a result, the specimen which was heat treated at 1000° C. for 12 hours exhibited the highest conductivity of $1.3\times10^{-3}$ S/cm at room temperature (Table 1, Example No. 1).

Example 2

As the starting materials, $NH_4H_2PO_4$, $TiO_2$, $Al(OH)_3$, $Ga_2O_3$ and $Li_2CO_3$ were used to produce a glass-ceramic by employing the same manner as in Example 1. The crystal phase which grew in specimens of this glass-ceramic was determined to be $Li_{1+x}(Al, Ga)_xTi_{2-x}(PO_4)_3$. The specimen which was heat treated at 950° C. for 12 hours exhibited the highest conductivity of $1.0\times10^{-3}$ S/cm (Table 1, Example No.2).

TABLE 1

(composition in mol %)

| | Examples | |
|---|---|---|
| No. | 1 | 2 |
| $P_2O_5$ | 39 | 39 |
| $TiO_2$ | 39 | 38 |
| $Al_2O_3$ | 8.5 | 6.5 |
| $Ga_2O_3$ | | 2.5 |
| $Li_2O$ | 13.5 | 14 |
| coductivity at room temperature (S/cm) | $1.3\times10^{-3}$ | $1.0\times10^{-3}$ |
| temperature of heat treatment (° C.) | 1000 | 950 |
| time of heat treatment (Hr) | 12 | 12 |

Example 3

As starting materials, $NH_4H_2PO_4$, $SiO_2$, $TiO_2$, $Al(OH)_3$ and $Li_2CO_3$ were used. These starting materials were weighed to constitute a composition of $32P_2O_5$-$8SiO_2$-$41TiO_2$-$5Al_2O_3$-$14Li_2O$ in mol %. The materials were mixed uniformly and then put in a platinum crucible and heated and melted in an electrical furnace. First, $CO_2$, $NH_3$ and $H_2O$ coming from the raw materials were evaporated at 700° C. Then the temperature was raised to 1450° C. and the materials were melted by heating them at this temperature for 1.5 hour. Thereafter, the melt was cast onto a stainless steel plate to form a uniform sheet glass. The glass was annealed at 550° C. for two hours for removing thermal stress of the glass.

The glass thus produced was cut into specimens each having the size of 20×20 mm. The specimens of glass were polished on both surfaces and subjected to heat treatment at a temperature of 800° C. for 12 hours and then at 1000° C. for 24 hours to produce a dense glass-ceramic. The crystal phase precipitated in the specimens was determined by the powder X-ray diffraction to be $Li_{1+x+y}Al_xTi_{2-x}Si_yP_{3-y}O_{12}$. The glass-ceramic exhibited a very high conductivity of $1.5\times10^{-3}$ S/cm at room temperature (Table 2, Example No. 3).

FIG. 1 shows an X-ray diffraction pattern of the glass-ceramic of Example 3.

Examples 4–8

Specimens of glass-ceramics were prepared in a manner similar to Example 3. The compositions and conductivities of these specimens as well as the composition and conductivity of Example 1 are shown in the following Tables 2 and 3.

TABLE 2

(composition in mol %)

| | Examples | | |
|---|---|---|---|
| No. | 3 | 4 | 5 |
| $P_2O_5$ | 32 | 33.5 | 30 |
| $SiO_2$ | 8 | 6 | 10 |
| $TiO_2$ | 41 | 42 | 40 |
| $Al_2O_3$ | 5 | 5 | 5 |
| $Ga_2O_3$ | | | |
| $Li_2O$ | 14 | 13.5 | 15 |
| coductivity at room temperature (S/cm) | 1.5 × $10^{-3}$ | 1.0 × $10^{-3}$ | 1.2 × $10^{-3}$ |

TABLE 3

(composition in mol %)

| | Examples | | |
|---|---|---|---|
| No. | 6 | 7 | 8 |
| $P_2O_5$ | 35 | 32 | 35 |
| $SiO_2$ | 4 | 8 | 4 |
| $TiO_2$ | 38 | 41 | 38 |
| $Al_2O_3$ | 8 | | 5 |
| $Ga_2O_3$ | | 5 | 3 |
| $Li_2O$ | 15 | 14 | 15 |
| coductivity at room temperature (S/cm) | 1.1 × $10^{-3}$ | 1.2 × $10^{-3}$ | 1.0 × $10^{-3}$ |

Example 9

Figure 2:
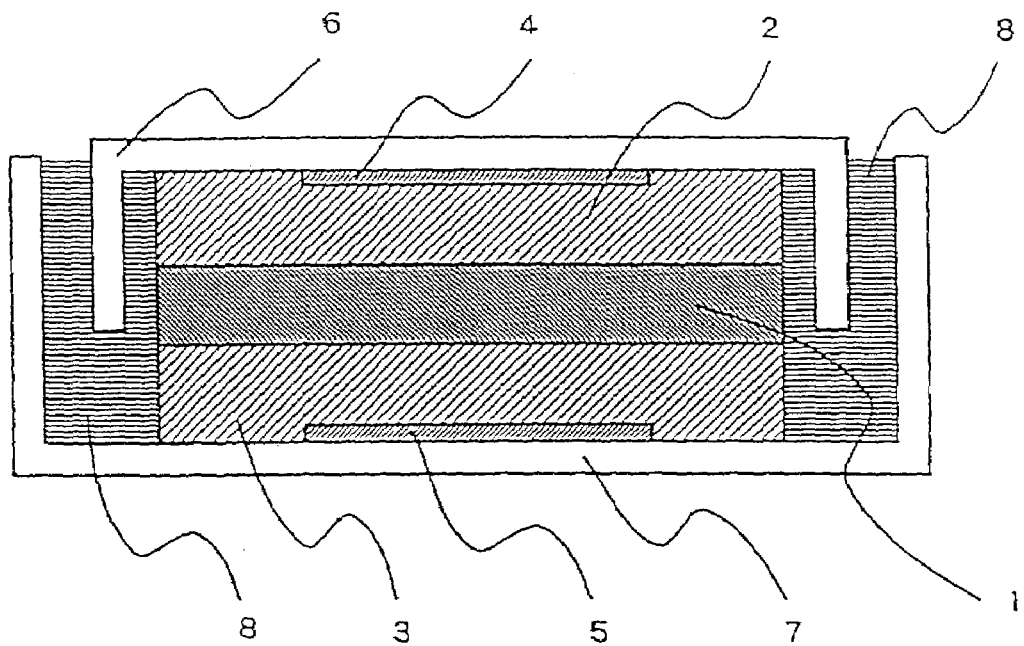
FIG. 2 is a sectional view of an example of a lithium cell using a lithium ion concuctive solid electrolyte.

As a typical example of a lithium electric cell, an example of flat type cell is shown in the sectional view of FIG. 2. The cell is composed of a negative electrode container 6, a negative electrode collector 4 constructed of a conductive thin film or a thin film made of aluminum or stainless steel, a negative electrode 2, a lithim ion conductive glass-ceramic layer 1, a positive electrode 3, a positive electrode collector 5 constructed of a conductive thin film or a thin film made of aluminum or stainless steel, a positive electrode container 7 and an insulating filler 8 made of an insulating material such as polypropylene. The positive and negative electrodes 2 and 3 are received in the case formed by the positive and negative electrode containers 6 and 7 in such a manner that these electrodes 2 and 3 oppose each other through the lithim ion conductive glass-ceramic layer 1. The positive electrode 3 is connected to the positive electrode container 7 through the positive electrode collector 5 and the negative electrode 2 is connected to the negative electrode container 6 through the negative electrode collector 4. Chemical energy produced in the cell can be collected as electric energy from terminals of the negative electrode container 6 and the positive electrode container 7.

In constructing the cell made according to the invention, various other materials which are conventionally used for forming a cell can be used except for the solid electrolyte portion.

The lithium ion conductive glass-ceramic layer must be sufficiently thin, i.e., 1 mm or less and preferably 0.5 mm or less. Many reports and proposals have been made about the material of the positive electrode 3 and it is typically made of $LiCoO_2$ or $Li_{1+x}V_3O_8$. Likewise, reports and proposals have been made about the material of the negative electrode 2 and it is typically made of $Li_4Ti_5O_{12}$ or carbon.

As to the positive and negative electrodes 2 and 3 formed on the opposite surfaces of the lithium ion conductive glass-ceramic layer 1 and the collectors 4 and 5 formed in the negative and positive electrodes 2 and 3, these component parts may be preformed respectively and stacked one after another to a composite cell. Alternatively, the positive and negative electrodes 2 and 3 and the collectors 4 and 5 may be formed sequentially by any of suitable known methods including ion spattering, CVD, screen printing, coating, sol-gel method, ion plating, ion beam evaporation and electron beam evaporation.

As a comparative example, a cell is composed in the same manner as in the above example except that the solid electrolyte is formed by mixing 1.7 mol of titanium oxide, 0.7 mol of lithium carbonate, 3.0 mol of ammonium phosphate and 0.2 mol of aluminum oxide in an agate mortar, press-forming the mixture to pellets and sintering the pellets at 900° C. for two hours, crushing the sintered pellets again in an agate mortar, press-forming the crushed material which has passed a shieve of 400 mesh to pellets again, sintering the pellets at 1000° C. for two hours and processing the sintered pellets to a thin plate.

Example 10

Figure 3:
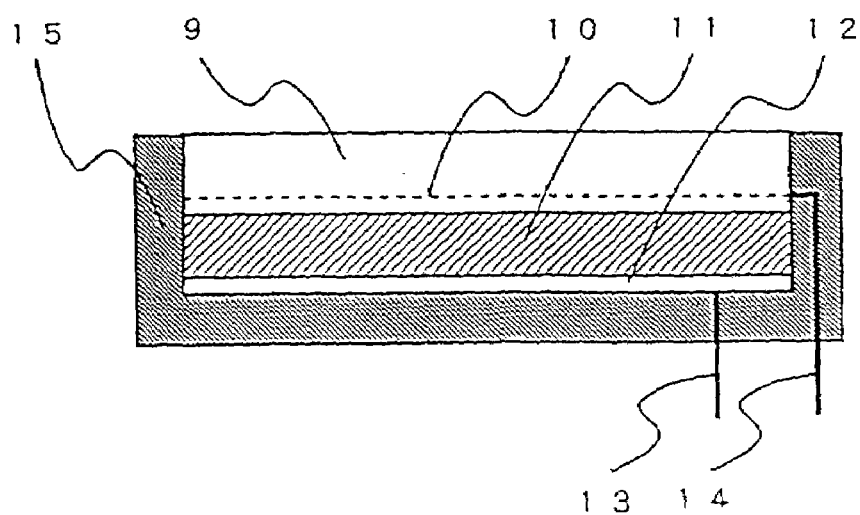
FIG. 3 is a sectional view showing an example of a gas sensor using a lithium ion conductive solid electrolyte.
Figure 4:
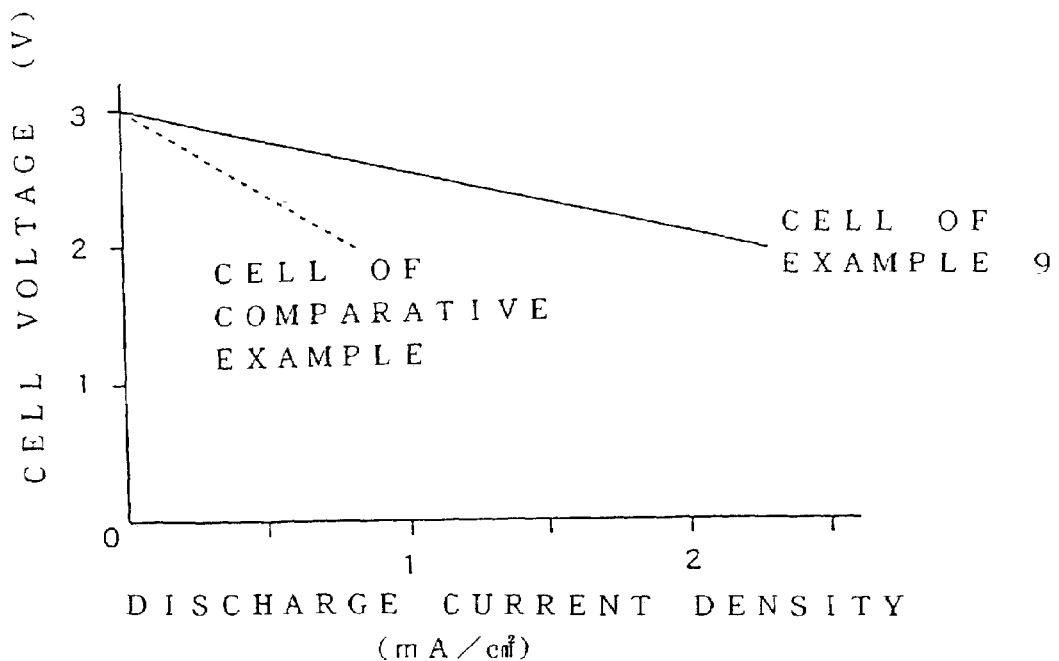
FIG. 4 is a graph showing an effective discharge characteristic of the cell shown in FIG. 2.
Figure 5:
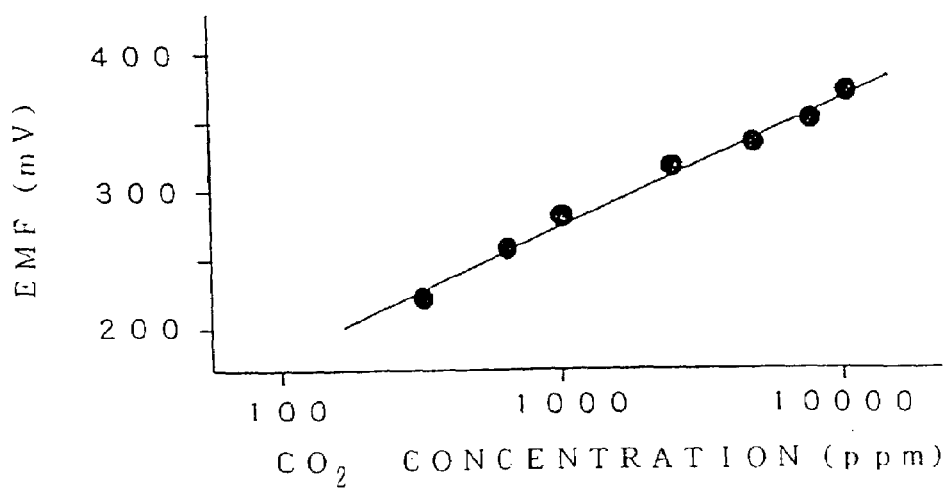
FIG. 5 is a graph showing an electromotive force characteristic by a carbonate gas partial pressure at room temperature of the gas sensor shown in FIG. 3.

As a typical example of a gas sensor, an example of a carbon dioxide gas sensor is shown in section in FIG. 3. The upper and lower surfaces of a lithium ion conductive glass-ceramic layer 11 are polished to provide the layer 11 having a thickness of 1 mm to 2 mm, preferably 1 mm or below and more preferably 0.5 mm or below. On one of the surfaces of the layer 11 (the upper surface in the illustrated example) is formed, by ion spattering, a layer of metal carbonate, preferably lithium carbonate or a mixture of lithium carbonate and other carbonate. A platinum mesh 10 to which a lead 14 is connected is disposed on the surface of this metal carbonate layer to form an electrode. Then, a layer 9 of metal carbonate is formed on the upper surface of the electrode 10 to fix the electrode 10. On the other surface (the lower surface in the illustrated example) of the lithium ion conductive layer 11 is formed, by evaporation, a platinum thin film to form an electrode 12 and a lead 13 is connected to the electrode 12. According to this sensor, an electromotive force corresponding to the concentration of carbon dioxide gas is produced between the two electrodes due to dissociation equilibrium of the carbonate by the carbon dioxide gas in a mixture gas including the carbon dioxide gas and, therefore, the concentration of the carbon dioxide gas can be detected by measuring this electromotive force.

Forming of the carbonate layer and the electrode layers is not limited to the above method but these layers may be formed by other known methods including CVD, screen printing, sol-gel method, ion plating, ion beam evaporation, MBE, vacuum evaporation and electron beam evaporation.

What is claimed is:

1. Lithium ion conductive glass-ceramics comprising in mol %:

| | |
|---|---|
| $P_2O_5$ | 38–40% |
| $TiO_2$ | 30–45% |

| | |
|---|---|
| $Al_2O_3$ | 5–15% |
| $Li_2O$ | 10–16% | and containing $Li_{1+x}Al_xTi_{2-x}(PO_4)_3$ (where 0<X<0.8) as a main crystal phase, said glass-ceramics being obtained by melting raw materials to a melt, casting the melt to a glass and subjecting the glass to heat treatment.

2. Lithium ion conductive glass-ceramics consisting essentially of in mol %:

| | |
|---|---|
| $P_2O_5$ | 38–40% |
| $TiO_2$ | 30–45% |
| $Al_2O_3$ | 5–15% |
| $Li_2O$ | 10–20% | and containing $Li_{1+x}Al_xTi_{2-x}(PO_4)_3$ (where 0<x<0.8) as a main crystal phase, said glass-ceramics being obtained by melting raw materials to a melt, casting the melt to a glass and subjecting the glass to heat treatment.

3. Lithium ion conductive glass-ceramics consisting essentially of in mol %:

| | |
|---|---|
| $P_2O_5$ | 26–40% |
| $SiO_2$ | 0.5–12% |
| $TiO_2$ | 32–45% |
| $Al_2O_3$ | 5–10% |
| $Li_2O$ | 10–18% | and containing $Li_{1+x+y}Al_xTi_{2-x}Si_yP_{3-y}O_{12}$ (where $0<X\leq0.4$ and $0<Y\leq0.6$) as a main crystal phase, said glass-ceramics being obtained by melting raw materials to a melt, casting the melt to a glass end subjecting the glass to heat treatment.

4. Lithium ion conductive glass-ceramics comprising in mol %:

| | |
|---|---|
| $P_2O_5$ | 26–40% |
| $SiO_2$ | 0.5–12% |
| $TiO_2$ | 32–45% |
| $Al_2O_3$ | 5–10% |
| $Li_2O$ | 10–18% | and containing $Li_{1+x+y}Al_xTi_{2-x}Si_yP_{3-y}O_{12}$ (where $0<X\leq0.4$ and $0<Y\leq0.6$) as a main crystal phase, said glass-ceramics being obtained by melting raw materials to a melt, casting the melt to a glass and subjecting the glass to heat treatment.

5. Lithium ion conductive glass-ceramics which consists in mol %:

| | |
|---|---|
| $P_2O_5$ | 26–40% |
| $SiO_2$ | 0.5–12% |
| $TiO_2$ | 32–45% |
| $Al_2O_3$ | 5–10% |
| $Li_2O$ | 10–18% | and containing $Li_{1+x+y}Al_xTi_{2-x}Si_yP_{3-y}O_{12}$ (where $0<X\leq0.4$ and $0<Y\leq0.6$) as a main crystal phase, said glass-ceramics being obtained by melting raw materials to a melt, casting the melt to a glass and subjecting the glass to heat treatment.

* * * * *